(12) United States Patent
Parchak et al.

(10) Patent No.: US 8,798,711 B2
(45) Date of Patent: Aug. 5, 2014

(54) SHIELDING OF CATHETER HANDLE

(75) Inventors: Yochai Parchak, Raanana (IL); Meir Bar-Tal, Zichron Ya'acov (IL); Meiron Atias, Moshav Shaar-Efreim (IL); Andres Claudio Altmann, Haifa (IL); Assaf Govari, Haifa (IL); Yaron Ephrath, Karkur (IL)

(73) Assignee: Biosense Webster, Inc.

( * ) Notice: Subject to any disclaimer, the term of this patent is extended or adjusted under 35 U.S.C. 154(b) by 1552 days.

(21) Appl. No.: 12/169,693

(22) Filed: Jul. 9, 2008

(65) Prior Publication Data

US 2008/0306380 A1 Dec. 11, 2008

Related U.S. Application Data

(63) Continuation-in-part of application No. 11/351,135, filed on Feb. 9, 2006, now Pat. No. 7,860,553.

(51) Int. Cl.
*A61B 5/05* (2006.01)

(52) U.S. Cl.
USPC ............ 600/407; 600/372; 600/424; 600/437

(58) Field of Classification Search
USPC ................................ 600/407, 372, 424, 437
See application file for complete search history.

(56) References Cited

U.S. PATENT DOCUMENTS

| 4,290,663 | A | 9/1981 | Fowler et al. |
|---|---|---|---|
| 5,391,199 | A | 2/1995 | Ben-Haim |
| 5,443,489 | A | 8/1995 | Ben-Haim |
| 5,515,853 | A | 5/1996 | Smith et al. |
| 5,558,091 | A | 9/1996 | Acker et al. |
| 5,785,658 | A | 7/1998 | Benaron et al. |
| 5,807,261 | A | 9/1998 | Benaron et al. |
| 5,868,664 | A | 2/1999 | Speier et al. |
| 5,944,022 | A | 8/1999 | Nardella |
| 5,983,126 | A | 11/1999 | Wittkampf |
| 6,019,725 | A | 2/2000 | Vesely et al. |
| 6,080,101 | A | 6/2000 | Tatsuno et al. |
| 6,172,499 | B1 | 1/2001 | Ashe |
| 6,177,792 | B1 | 1/2001 | Govari et al. |
| 6,226,547 | B1 | 5/2001 | Lockhart et al. |
| 6,246,898 | B1 | 6/2001 | Vesely et al. |
| 6,266,551 | B1 | 7/2001 | Osadchy |
| 6,370,411 | B1 | 4/2002 | Osadchy |
| 6,456,864 | B1 | 9/2002 | Swanson |

(Continued)

FOREIGN PATENT DOCUMENTS

| EP | 0571225 A | 11/1993 |
|---|---|---|
| JP | 11221287 A | 8/1999 |
| WO | WO 03/101534 A1 | 12/2003 |

OTHER PUBLICATIONS

EP Search Report #EP 07 25 0514 dated May 14, 2007.

(Continued)

*Primary Examiner* — Unsu Jung
*Assistant Examiner* — Joel Lamprecht

(57) ABSTRACT

Electrical apparatus includes a probe, having a proximal end and a distal end. The probe includes a sensor, which outputs a sensor signal, and a first connector at the proximal end of the probe, electrically coupled at least to the sensor. A probe adapter includes a second connector, which is arranged to mate with the first connector, and a third connector, for coupling to a console. A shield includes a material of high magnetic permeability, which is configured to enclose an internal volume containing the first and second connectors when the probe is connected to the probe adapter.

12 Claims, 4 Drawing Sheets

(56) References Cited

U.S. PATENT DOCUMENTS

| | | |
|---|---|---|
| 6,626,902 B1 | 9/2003 | Kucharczyk et al. |
| 6,690,963 B2 | 2/2004 | Ben-Haim et al. |
| 6,711,429 B1 | 3/2004 | Gilboa et al. |
| 6,774,624 B2 | 8/2004 | Anderson et al. |
| 6,788,967 B2 | 9/2004 | Ben-Haim et al. |
| 6,980,921 B2 | 12/2005 | Anderson et al. |
| 7,090,639 B2 | 8/2006 | Govari |
| 2004/0254458 A1 | 12/2004 | Govari |
| 2007/0185397 A1 | 8/2007 | Govari et al. |

OTHER PUBLICATIONS

EP Search Report #EP 09 25 1760 dated Sep. 11, 2009.

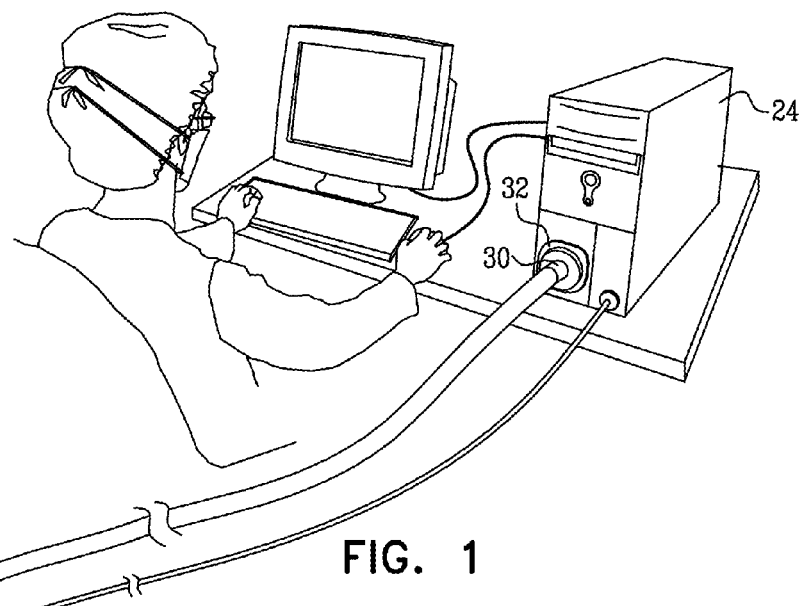
FIG. 1
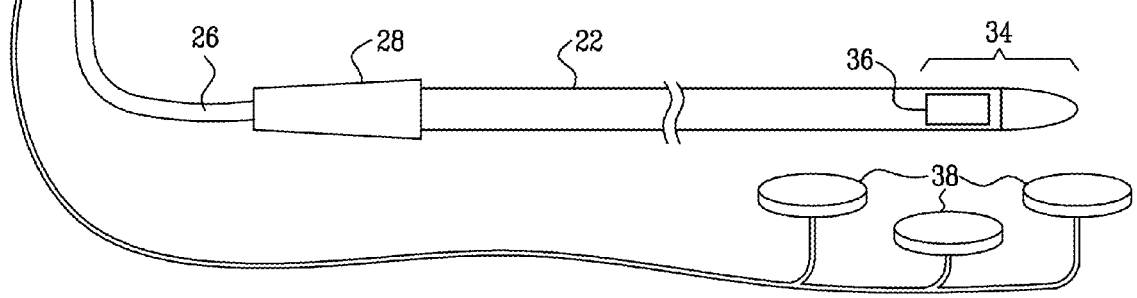
FIG. 2
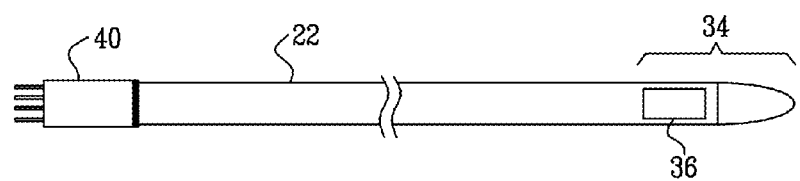

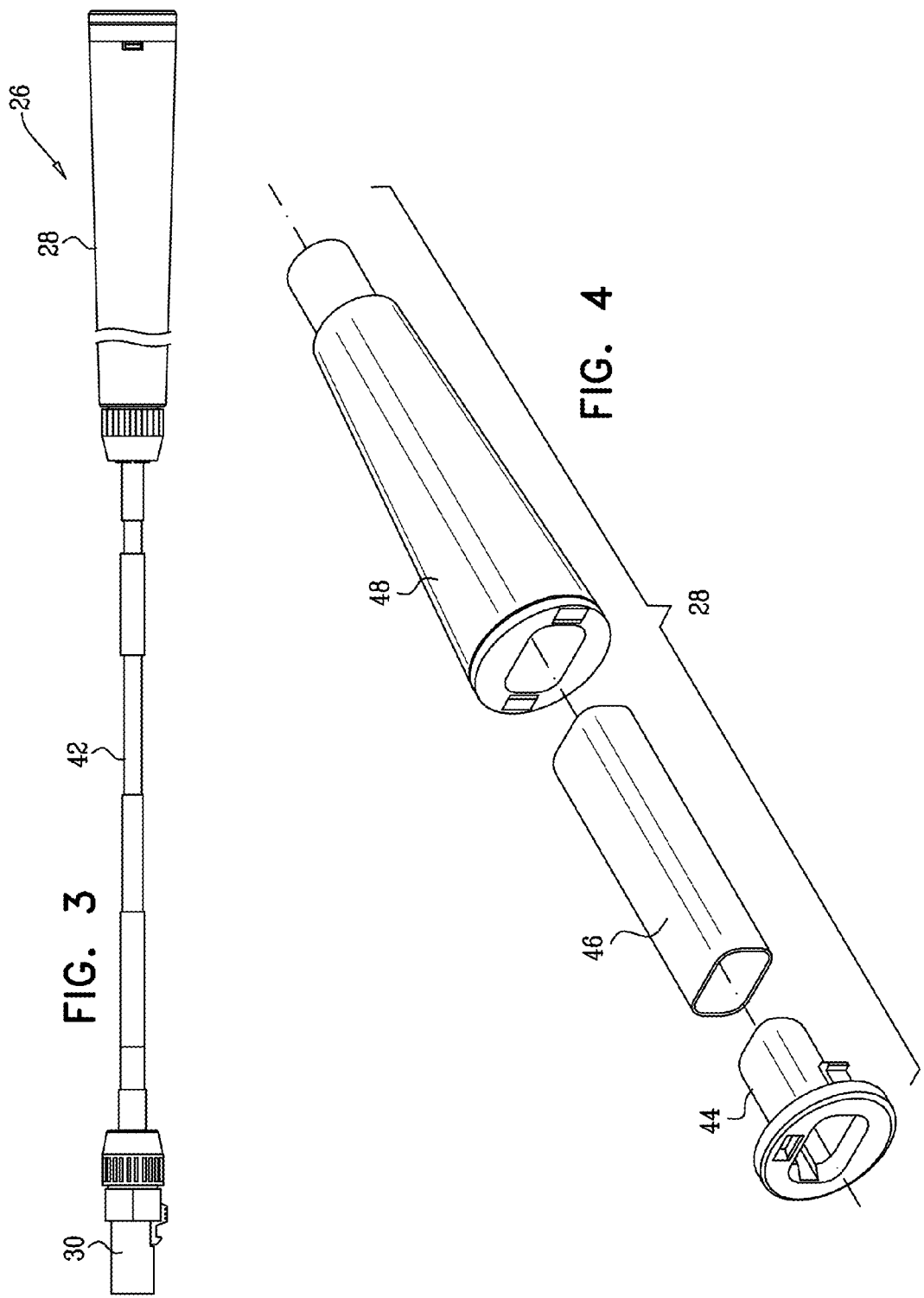

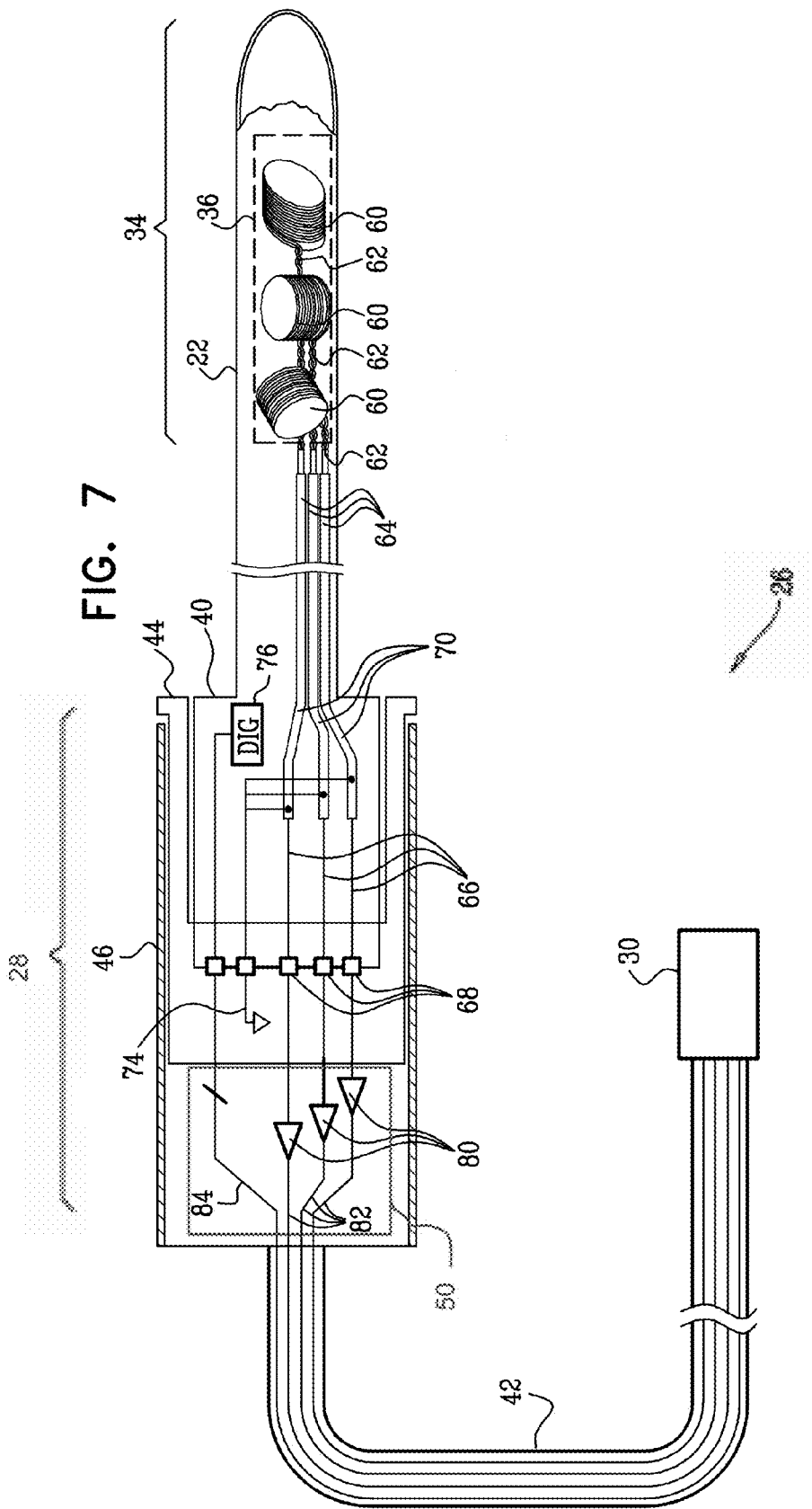

SHIELDING OF CATHETER HANDLE

CROSS-REFERENCE TO RELATED APPLICATION

This application is a continuation-in-part of U.S. patent application Ser. No. 11/351,135, filed Feb. 9, 2006 now U.S. Pat. No. 7,860,553, and published as US 2007/0185397 A1, whose disclosure is incorporated herein by reference.

FIELD OF THE INVENTION

The present invention relates generally to systems for medical diagnosis and treatment, and specifically to shielding of probes and sensors that are used in such systems against magnetic interference.

BACKGROUND OF THE INVENTION

Tracking the position of probes within the body is required for many medical procedures. For example, various systems have been developed for determining the position coordinates of an object in the body based on magnetic field sensing. These systems use sensors affixed to the object to measure the relative strengths of externally-generated magnetic fields and to derive from these measurements the position of the object. Methods for magnetic-based position sensing are disclosed, for example, in U.S. Pat. Nos. 5,391,199, 5,443,489, and 6,788,967 to Ben-Haim, in U.S. Pat. No. 6,690,963 to Ben-Haim, et al., in U.S. Pat. No. 5,558,091 to Acker et al., in U.S. Pat. No. 6,172,499 to Ashe, and in U.S. Pat. No. 6,177,792 to Govari.

The above-mentioned US 2007/0185397 describes methods for generating, storing and computing calibration information with respect to an invasive medical probe, such as a catheter. The probe connects via a suitable mating connector to an adapter, which in turn connects, via another mating connector, to a console. The probe comprises a sensor, such as a magnetic position sensor, and a probe microcircuit, which stores sensor calibration data. The adapter comprises a signal processing circuit for processing the signal that is output by the sensor. The adapter also comprises its own microcircuit, which stores calibration data with respect to the signal processing circuit. A microcontroller in the adapter computes combined calibration data based on the data from both of the microcircuits. Signal analysis circuitry in the console receives the processed signal and analyzes this signal using the combined calibration data provided by the probe adapter.

U.S. Pat. No. 4,290,663, to Fowler et al., describes a method of interconnecting screened cables. This patent states that reduction of magnetic reluctance of the magnetic path between inner and outer surfaces of the screen in the region of the interconnection decreases external interference to the screened cable. Mu-metal can be used to reduce the magnetic reluctance.

SUMMARY OF THE INVENTION

Some types of electrical devices must operate under strong magnetic fields, such as the magnetic fields that are used in the above-mentioned magnetic position sensing systems. Care must be taken in the design and handling of the electrical wires in such devices to avoid picking up interference from the magnetic fields.

For this purpose, in an embodiment described in the above-mentioned US 2007/0185397, the mating connectors of the catheter and the adapter comprise magnetic shielding, using Mu-metal, for example, to reduce magnetic interference with the weak signals on the pins of the connectors. The inventors have discovered, furthermore, that for effective protection against interference, it is helpful that the circuit elements that are susceptible to magnetic interference, such as exposed pins and associated wires in a connector, be entirely contained in a volume that is enclosed by the shielding, without open seams through which magnetic fields may leak.

There is therefore provided, in accordance with an embodiment of the present invention, electrical apparatus, including:

a probe, having a proximal end and a distal end, the probe including a sensor, which outputs a sensor signal, and a first connector at the proximal end of the probe, electrically coupled at least to the sensor;

a probe adapter, including a second connector, which is arranged to mate with the first connector, and a third connector, for coupling to a console; and a shield, including a material of high magnetic permeability, which is configured to enclose an internal volume containing the first and second connectors when the probe is connected to the probe adapter.

In a disclosed embodiment, the material is a Mu-metal, and the shield has a unitary, tubular form, which defines the internal volume.

In some embodiments, the probe adapter includes at least one amplifier, which is contained in the internal volume and is coupled to process the sensor signal so as to output a amplified signal via the third connector to the console.

In one embodiment, the sensor includes a position sensor, which is operative to generate the sensor signal responsively to a magnetic field applied externally to the body. The probe may include a catheter, whose distal end is configured for insertion into a heart of the subject.

In some embodiments, the probe includes a twisted pair of wires, which are coupled to convey the sensor signal from the sensor to the first connector, and the wires in the twisted pair are separated only within the internal volume of the shield for connection to respective pins of the first connector.

In a disclosed embodiment, the apparatus includes a handle, which contains the second connector and the shield, and the proximal end of the probe is configured to be plugged into and removed from the handle.

There is also provided, in accordance with an embodiment of the present invention, a method for producing an electrical device, including:

providing a probe, having a proximal end and a distal end, which includes a sensor, which outputs a sensor signal, and a first connector at the proximal end of the probe, electrically coupled at least to the sensor;

providing a second connector, for use in a probe adapter to mate with the first connector;

coupling a third connector to connect the probe adapter to a console; and configuring a shield, including a material of high magnetic permeability, so as to enclose an internal volume containing the first and second connectors when the probe is connected to the probe adapter.

The present invention will be more fully understood from the following detailed description of the embodiments thereof, taken together with the drawings in which:

BRIEF DESCRIPTION OF THE DRAWINGS

FIG. 1 is a schematic, pictorial illustration of a catheter-based medical system, in accordance with an embodiment of the present invention;

FIG. 2 is a schematic side view of a catheter, in accordance with an embodiment of the present invention;

FIG. 3 is a schematic side view of an adapter for connecting a catheter to a console, in accordance with an embodiment of the present invention;

FIG. 4 is a schematic, pictorial illustration showing an exploded view of parts of a connector assembly, in accordance with an embodiment of the present invention;

FIG. 7 is a block diagram that schematically shows electrical components of a catheter and adapter, in accordance with an embodiment of the present invention.

DETAILED DESCRIPTION OF EMBODIMENTS

Figure 5:
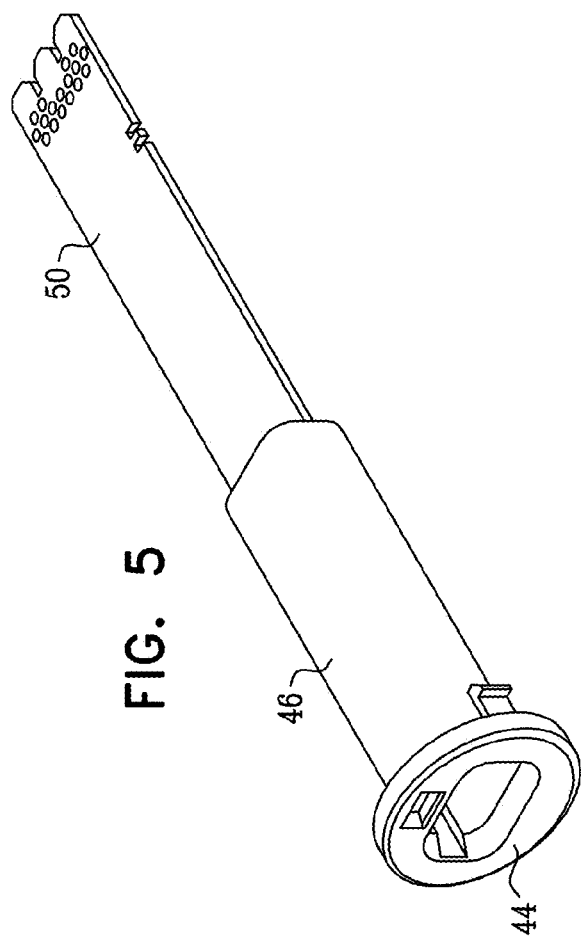
FIG. 5 is a schematic, pictorial illustration showing internal components of a connector assembly, in accordance with an embodiment of the present invention.

FIG. 1 is a schematic, pictorial illustration of a system 20 for cardiac catheterization, in accordance with an embodiment of the present invention. System 20 may be based, for example, on the CARTO™ system, produced by Biosense Webster Inc. (Diamond Bar, Calif.). This system comprises an invasive probe in the form of a catheter 22 and a control console 24.

Catheter 22 is typically provided to users as a disposable unit, which mates with a reusable adapter 26 via a connector assembly 28, which is described in detail hereinbelow. (The connector assembly may also serve as a handle, for use by a practitioner in inserting and manipulating the catheter within the patient's body.) Adapter 26 terminates in a connector 30, typically a plug, that mates with a corresponding connector 32, such as a receptacle, on console 24. In the context of the present patent application and in the claims, the term "connector" is used in the conventional sense, to mean any sort of electrical plug or similar device that can be readily connected and disconnected in the field without technical operations such as soldering or crimping.

Catheter 22 comprises an insertion tube whose distal end 34 is designed to be passed through the vascular system and into a chamber of the heart. The catheter contains a position sensor 36, which is used in determining position coordinates of distal end 34. In the CARTO system, the position sensor comprises three coils (shown below in FIG. 7), which output signals in response to magnetic fields that are applied by field generator coils 38. These fields are typically in the range of several hundred to several thousand Hertz, although lower or higher frequencies may be used, as well. The signals output by the position sensor are typically amplified by amplifiers in connector assembly 28, as described hereinbelow. Console 24 processes the amplified signals to determine the coordinates of the distal end of the catheter. Further details of the theory and operation of magnetic position sensing systems of this type are provided in the patents cited in the Background of the Invention.

Distal end 34 of catheter 22 may also comprise one or more functional elements (not shown in the figures) for performing therapeutic and/or diagnostic functions. For example, the functional elements may comprise an electrode or an ultrasound transducer.

In designing system 20 (and likewise other types of medical probes that must operate in an environment of strong magnetic fields), care should be taken to avoid picking up interference in the wires carrying the signals from the sensors at distal end 34 of catheter 22 to the amplifier circuits in connector assembly 28 and/or in console 24. Field generator coils 38 radiate strong fields in order to enable the position tracking system to achieve sufficient signal/noise ratio, with very small sensor coils in the catheter, to provide accurate position measurements. Long wires leading from the sensor coils to the proximal end of the catheter pass through these strong fields, and any loops in the wires will pick up interference. To minimize this interference, the coils are typically connected to the amplifier circuits by twisted pairs of thin wires running through the catheter with a high twist rate. The wires are untwisted and separated as close as possible to the input pins of the amplifiers in order to minimize the area that can pick up the electromagnetic field.

Nevertheless, given the strength of the magnetic fields and the weakness of the signals output by sensor 36, even minimal pickup of the magnetic fields at the input to the amplifiers can result in serious errors in the position coordinates of distal end 34. Embodiments of the present invention address this problem by incorporating a material with high magnetic permeability (i.e., with relative permeability of 1000 or greater) in connector assembly 28, as described in detail hereinbelow. The inventors have found that Mu-metal gives good results in this regard. This sort of shielding is important particularly in protecting position signals from magnetic interference, but it may also be used, additionally or alternatively, in protecting signals associated with functional elements of other types. Furthermore, although the present embodiment relates specifically to a cardiac catheter, the principles of the present invention may similarly be applied to other types of medical probes.

Reference is now made to FIGS. 2-4, which schematically show details of catheter 22 and adapter 26, particularly in regard to connector assembly 28, in accordance with an embodiment of the present invention. FIGS. 2 and 3 are side views of the catheter and the adapter, respectively, while FIG. 4 is an exploded view showing parts of the connector assembly. As shown in these figures, catheter 22 comprises a connector 40 at its proximal end, which is inserted into a receptacle 44 in connector assembly 28. The receptacle is connected via a cable 42 to connector 30, which plugs into console 24, as noted above. A Mu-metal shield 46 slides over and encloses receptacle 44, and a shell 48 slides over and covers the shield, resulting in the appearance shown in FIG. 3. Shell 48 comprises a suitable insulating material, typically a plastic, such as polybutylene terephthalate (PBT).

Mu-metal, as is known in the art, is a nickel-iron alloy, which undergoes a special annealing process that results in very high magnetic permeability ($\mu$). Shield 46 is made in the form of a tube, with an overlapping, welded seam, so that the tube behaves as a unitary sheath without any discontinuities along its length through which electromagnetic fields may leak. Mu-metal parts of this sort are available to order from a number of suppliers, including MuShield (Londonderry, N.H.). Shield 46 defines and encloses an internal volume, contained within the tube, in which external magnetic fields are strongly attenuated, so that wires and other electrical components are protected from magnetic interference. The inventors have found that within this protected volume, the magnetic fields are reduced by three orders of magnitude relative to the field strength outside the volume. Although the ends of the tube are open, boundary conditions constrain the field to drop sharply from the ends of the tube toward the center, where the connector itself is located.

Figure 6:
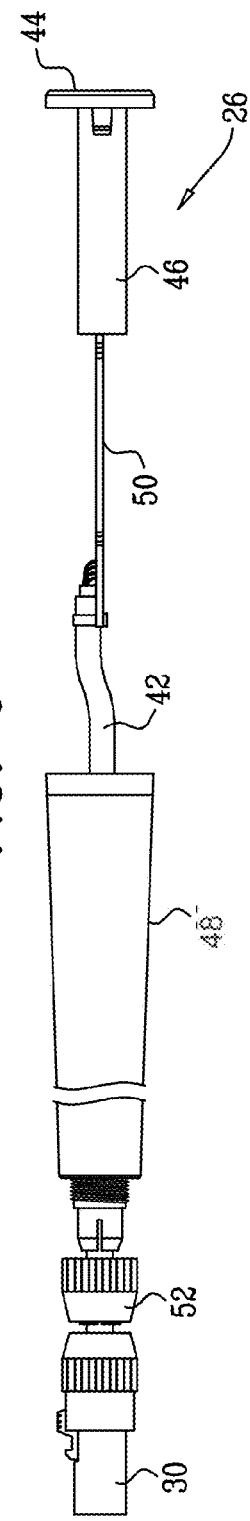
FIG. 6 is a schematic side view of an adapter at a stage of production, in accordance with an embodiment of the present invention.

FIGS. 5 and 6 schematically show further details of the production of adapter 26, in accordance with an embodiment of the present invention. FIG. 5 is a pictorial illustration showing internal components of connector assembly 28 at one stage of production, while FIG. 6 is a side view of adapter 26 at a later stage of production. In these figures, shield 46 has been slid over the rear side of receptacle 44 (the side opposite the opening, at the left side in FIGS. 4 and 5, into which connector 40 is inserted), and has been fastened in place, using a suitable glue, for example.

Prior to inserting the receptacle into the shield, a miniature printed circuit board 50 is connected, typically by soldering, to the pins of receptacle 44. The printed circuit board has pads for accommodating certain circuit components and traces for connecting the pins and the components, as shown in FIG. 7. Cable 42 is soldered to the appropriate traces on board 50. Cover 48 is then slid forward over the cable from the location shown in FIG. 6 so that it covers shield 46. A strain-relief nut 52 is tightened over a thread at the proximal end of cover 48 in order to hold the cover in place.

After insertion of connector 40 into receptacle 44, cover 48 of connector assembly 28 can be used conveniently by the operator of system 20 as a handle for catheter 22. When the procedure is finished, the operator simply unplugs the catheter from the handle and, typically, disposes of the catheter. Adapter 28, on the other hand, may be reused in subsequent procedures and typically does not require sterilization between procedures, since only the (disposable) catheter comes into contact with the patient.

FIG. 7 is a block diagram that schematically shows electrical components of catheter 22 and adapter 26, in accordance with an embodiment of the present invention. The figure particularly shows details of sensor 36 and of the connections and components that are contained in the shielded volume that is defined and enclosed by shield 46 in connector assembly 28.

Sensor 36 comprises three non-concentric coils 60, which may be aligned along mutually-orthogonal axes. Coil wires 62, wound in tightly-twisted pairs, are connected via cables 64 running through catheter 22 to pins 66 of connector 40. (For the sake of simplicity, only a single pin is connected to each cable in FIG. 7, but in actuality a respective pair of pins may be connected to the pair of twisted wires in each cable.) Typically, the twisted-pair wires are unwound only in connector 40, which is contained in the shielded volume of shield 46. Pins 66 mate with sockets 68 of receptacle 44. Typically, cables 64 comprise shields 70, which are connected via a ground pin 72 of connector 40 to a ground line 74 in receptacle 44.

Sockets 68 connect the outputs of coils 60 to respective amplifiers 80, which may be mounted on board 50, as described above. Amplifiers 80 typically comprise low-noise, low-distortion instrumentation amplifiers, such as the INA103 amplifier produced by Burr-Brown (Tucson, Ariz.). For applications in magnetic position sensing, as in system 20, the amplifiers are set and calibrated for high gain, typically in the range of 2000. Amplifiers 80 and the traces leading to their inputs are likewise protected by shield 46. The amplified signals produced by amplifiers 80 pass through conductors 82 to cable 42, which conveys the signals via connector 30 to console 24. Because these amplified signals are considerably stronger than the output signals from coils 60, they are much less susceptible to magnetic interference. Alternatively, in other configurations, the amplifiers may be located elsewhere (in console 24, for example), and only connector 40 and receptacle 44 are contained in shield 46. The console typically filters, digitizes and processes the signals in order to compute the location and orientation coordinates of distal end 34 of catheter 22.

Catheter 22 may comprise a digital component 76, such as a memory component, which stores identification and calibration information regarding the catheter. Digital information from component 76 is conveyed via a bus 84 and cable 42 to console 24. Alternatively or additionally, connector assembly 28 may comprise a digital section (not shown), which receives and processes the information stored by digital component 76, possibly along with other information stored in this digital section, and may then pass the results to the console. This sort of arrangement is described in the above-mentioned US 2007/0185397.

Although the embodiments described above relate specifically to magnetic position sensors and systems, the principles of the present invention may similarly be applied in preventing magnetic interference with signals that are output by other types of sensors that must operate in strong magnetic fields. Examples of such sensors may include, without limitation, impedance-based and ultrasonic position sensors, as well as sensing electrodes, chemical sensors, temperature sensors, pressure sensors and ultrasonic transducers. Furthermore, although these embodiments relate specifically to cardiac catheters, the methods of shielding that are described above may likewise be used in connecting sensing probes of other types to respective consoles.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Electrical apparatus, comprising:
a probe, having a proximal end and a distal end, the probe comprising:
a sensor, which outputs a sensor signal; and
a first connector at the proximal end of the probe, electrically coupled at least to the sensor;
a probe adapter, comprising:
a second connector at a distal end of the probe adapter, which is arranged to mate with the first connector of the probe; and
a third connector located proximal from the first connector and the second connector, and coupled to a console; and
a shield, comprising a mu-metal material of high magnetic permeability, the shield being made of unitary tubular form which is configured to enclose an internal volume containing the first connector and second connectors when the probe is connected to the probe adapter, the unitary tubular form of the shield preventing leakage of electromagnetic fields from the first connector and the second connector when the probe is connected to the probe adapter.

2. The apparatus according to claim 1, wherein the sensor further comprises at least one amplifier, which is contained in the internal volume and is coupled to process the sensor signal so as to output an amplified signal via the third connector to the console.

3. The apparatus according to claim 1, wherein the sensor comprises a position sensor, which is operative to generate the sensor signal responsively to a magnetic field applied externally to the body.

4. The apparatus according to claim 1, wherein the probe comprises a catheter, and wherein the distal end is configured for insertion into a heart of the subject.

5. The apparatus according to claim 1, wherein the probe comprises a twisted pair of wires, which are coupled to convey the sensor signal from the sensor to the first connector, and wherein the wires in the twisted pair are separated only within the internal volume of the shield for connection to respective pins of the first connector.

6. The apparatus according to claim 1, and further comprising a handle, which contains the second connector and the shield, and wherein the proximal end of the probe is configured to be plugged into and removed from the handle.

7. A method for producing an electrical device, comprising:
providing a probe, having a proximal end and a distal end, which comprises a sensor, which outputs a sensor signal, and a first connector at the proximal end of the probe, electrically coupled at least to the sensor;
providing a second connector, for use in a probe adapter to mate with the first connector of the probe;
coupling a third connector located proximal of the second connector to connect the probe adapter to a console; and
configuring a shield, comprising a mu-metal material of high magnetic permeability and being made of unitary tubular form, so as to enclose an internal volume containing the first connector and the second connector& when the probe is connected to the probe adapter, the unitary tubular form of the shield preventing leakage of electromagnetic fields from the first connector and the second connector when the probe is connected to the probe adapter.

8. The method according to claim 7, and comprising coupling at least one amplifier in the probe adapter to the second connector so as to receive and process the sensor signal in order to output a amplified signal via the third connector to the console, wherein the at least one amplifier is contained in the internal volume of the shield.

9. The method according to claim 7, wherein the sensor comprises a position sensor, which is operative to generate the sensor signal responsively to a magnetic field applied externally to the body.

10. The method according to claim 7, where providing the probe further comprises coupling a twisted pair of wires to convey the sensor signal from the sensor to the first connector, and separating the wires in the twisted pair for connection to the respective pins of the first connector only within a part of the probe that is within the internal volume of the shield.

11. The method according to claim 7, wherein providing the probe comprises coupling a twisted pair of wires to convey the sensor signal from the sensor to the first connector, and separating the wires in the twisted pair for connection to respective pins of the first connector only within a part of the probe that is within the internal volume of the shield.

12. The method according to claim 7, and further comprising:
assembling a handle over the second connector and the shield;
plugging the proximal end of the probe into the handle prior to performing a medical procedure using the probe; and
removing the proximal end of the probe from the handle after performing the medical procedure.

* * * * *